United States Patent
Matheny et al.

(10) Patent No.: US 9,700,654 B2
(45) Date of Patent: Jul. 11, 2017

(54) EXTRACELLULAR MATRIX (ECM) STRUCTURES FOR TISSUE REGENERATION

(71) Applicants: Robert G Matheny, Norcross, GA (US); Craig N Ferrante, Dunstable (GB)

(72) Inventors: Robert G Matheny, Norcross, GA (US); Craig N Ferrante, Dunstable (GB)

(73) Assignee: CorMatrix Cardiovascular, Inc., Roswell, GA (US)

( * ) Notice: Subject to any disclaimer, the term of this patent is extended or adjusted under 35 U.S.C. 154(b) by 106 days.

(21) Appl. No.: 14/452,794

(22) Filed: Aug. 6, 2014

(65) Prior Publication Data

US 2015/0359942 A1 Dec. 17, 2015

Related U.S. Application Data

(63) Continuation-in-part of application No. 14/306,368, filed on Jun. 17, 2014, now Pat. No. 9,333,277, and a continuation of application No. 13/033,102, filed on Feb. 23, 2011, now Pat. No. 8,758,448.

(51) Int. Cl.
| | | |
|---|---|---|
| *A61F 2/00* | (2006.01) | |
| *A61K 35/12* | (2015.01) | |
| *A61K 35/37* | (2015.01) | |
| *C07K 1/00* | (2006.01) | |
| *A61L 27/56* | (2006.01) | |
| *A61L 27/54* | (2006.01) | |
| *A61K 38/18* | (2006.01) | |
| *A61K 35/28* | (2015.01) | |
| *A61L 27/38* | (2006.01) | |
| *A61K 35/545* | (2015.01) | |
| *A61K 9/70* | (2006.01) | |
| *A61F 2/02* | (2006.01) | |
| *A61K 35/38* | (2015.01) | |
| *A61L 27/36* | (2006.01) | |

(52) U.S. Cl.
CPC ............ *A61L 27/56* (2013.01); *A61K 9/7007* (2013.01); *A61K 35/12* (2013.01); *A61K 35/28* (2013.01); *A61K 35/545* (2013.01); *A61K 38/18* (2013.01); *A61L 27/3633* (2013.01); *A61L 27/3834* (2013.01); *A61L 27/54* (2013.01); *A61F 2/02* (2013.01); *A61F 2210/0076* (2013.01); *A61K 35/38* (2013.01); *A61L 27/3683* (2013.01); *A61L 2300/414* (2013.01); *A61L 2430/00* (2013.01)

(58) Field of Classification Search
CPC ... A61F 2/02; A61F 2210/0076; A61K 35/12; A61K 35/38; A61K 38/18; A61L 27/3633; A61L 27/3683; A61L 27/54; A61L 27/56; A61L 2300/414
USPC .......................... 424/423, 551, 572; 530/350
See application file for complete search history.

(56) References Cited

U.S. PATENT DOCUMENTS

| | | |
|---|---|---|
| 2002/0173033 A1 | 11/2002 | Hammerick et al. |
| 2003/0036797 A1 | 2/2003 | Malaviya et al. |
| 2003/0125295 A1* | 7/2003 | Mintz et al. |
| 2010/0028396 A1 | 2/2010 | Ward et al. |
| 2012/0016491 A1* | 1/2012 | Matheny |
| 2012/0135045 A1 | 5/2012 | Nixon et al. |
| 2012/0303117 A1 | 11/2012 | Matheny |
| 2013/0144356 A1* | 6/2013 | Horn et al. |

* cited by examiner

*Primary Examiner* — Shin Lin Chen
(74) *Attorney, Agent, or Firm* — Francis Law Group

(57) ABSTRACT

A multi-sheet extracellular matrix (ECM) structure for tissue regeneration, the ECM structure having joined first and second ECM sheet members and an agent dispersal network disposed between the sheets, the dispersal network being configured to receive and transfer a bioactive agent through the network and, when the ECM structure is attached to tissue, administer the bioactive agent to the tissue.

8 Claims, 6 Drawing Sheets

EXTRACELLULAR MATRIX (ECM) STRUCTURES FOR TISSUE REGENERATION

CROSS-REFERENCE TO RELATED APPLICATIONS

This application is a continuation-in-part of co-pending U.S. patent application Ser. No. 14/306,368, filed on Jun. 17, 2014, which is a continuation of co-pending U.S. patent application Ser. No. 13/033,102, filed on Feb. 23, 2011, now U.S. Pat. No. 8,258,448, which is a continuation of co-pending U.S. patent application Ser. No. 12/394,914, filed on Feb. 27, 2009, now abandoned, which is a continuation of U.S. patent application Ser. No. 11/747,004, filed on May 10, 2007, now abandoned, which applications are hereby incorporated herein by reference in their entireties.

FIELD OF THE INVENTION

The present invention relates generally to grafts for repairing damaged tissue. More particularly, the present invention relates to multi-sheet articles comprising extracellular matrix (ECM) having an agent dispersal network therein.

BACKGROUND OF THE INVENTION

Tissue regeneration has been accomplished by using extracellular matrix (ECM) material derived from various mammalian tissues. Some of these mammalian tissues that have been described in patent literature include small intestine submucosa (SIS), liver basement membrane (LBM), urinary bladder submucosa (UBS) and stomach submucosa (SS). See U.S. Pat. No. 5,554,389, U.S. Pat. No. 4,902,508 and U.S. Pat. No. 5,281,422. Enamel matrices, which are the extracellular matrix around forming teeth, are described in U.S. Pat. No. 7,033,611.

Extracellular matrices from these tissues have been isolated and dried to become solid materials (sheets and particulates). Particulate forms can be rehydrated in a suitable buffer to become fluidized or emulsive forms.

Single and multi-sheet laminate structures comprising ECM are presently employed for tissue grafting, wound healing, and tissue regenerative purposes.

A drawback of the conventional single and multi-sheet structures is that they have limited capability to disperse a bioactive or pharmacological agent or composition therefrom.

It would thus be desirable to provide ECM based graft structures that are capable of controlled dispersal of bioactive and pharmacological agents and compositions therefrom.

It is therefore an object of the invention to provide ECM based graft structures that are capable of controlled dispersal of bioactive and pharmacological agents and compositions therefrom.

It is another object of the present invention to provide ECM based graft structures that are capable of administering a bioactive and pharmacological agents and compositions to host tissue and, thereby produce a desired biological and/or therapeutic effect.

It is another object of the present invention to provide ECM based graft structures that can effectively replace or improve biological functions or promote the growth of new tissue in a subject.

It is another object of the present invention to provide ECM based graft structures that induce host tissue proliferation, bioremodeling and regeneration of new tissue and tissue structures with site-specific structural and functional properties.

It is another object of the present invention to provide vascular grafts that are capable of administering a pharmacological agent to host tissue and, thereby produce a desired biological and/or therapeutic effect.

SUMMARY OF THE INVENTION

The present invention is directed to extracellular matrix (ECM) structures for inducing tissue regeneration.

In some embodiments of the invention, the ECM structure comprises a folded sheet member having an internal agent dispersal network disposed between the folded sheet that is configured to receive and disperse at least one bioactive agent or composition therefrom.

In a preferred embodiment of the invention, the ECM structure comprises a multi-sheet member having an internal agent dispersal network disposed between the two sheets that is configured to receive and disperse at least one bioactive agent or composition therefrom.

In a preferred embodiment, each sheet comprises ECM selected from the group comprising small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, cardiac extracellular matrix, e.g., pericardium and/or myocardium, kidney extracellular matrix, pancreas extracellular matrix, lung extracellular matrix, and combinations thereof.

The ECM material can also comprise collagen from mammalian sources.

In some embodiments, the agent dispersal network comprises mating channels between two ECM sheets.

In some embodiments, the agent dispersal network comprises a separate network member that is disposed between two ECM sheets.

In some embodiments the network member comprises a biodegradable material.

In some embodiments, the biodegradable material comprises a biodegradable polymeric material selected from the group comprising polyhydroxyalkonates (PHAs), polylactides (PLLA) and polyglycolides (PLGA) and their copolymers. for example poly($\epsilon$-caprolactone-co-glycolide), polyanhydrides, and like polymers.

In some embodiments, the ECM structure comprises at least one exogenously added biologically active agent.

In some embodiments of the invention, the biologically active agent comprises a growth factor selected from the group comprising a platelet derived growth factor (PDGF), epidermal growth factor (EGF), transforming growth factor alpha (TGF-$\alpha$), transforming growth factor beta (TGF-$\beta$), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNA-$\alpha$), and placental growth factor (PLGF).

In some embodiments of the invention, the biologically active agent comprises a cell selected from the group comprising human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some embodiments of the invention, the biologically active agent is selected from the group comprising collagen (types I-V), proteoglycans, glycosaminoglycans (GAGs), glycoproteins, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

In some embodiments, the ECM structure comprises at least one exogenously added pharmacological agent.

In some embodiments of the invention, the pharmacological agent is selected from the group comprising antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a Class I, II, III or IV anti-arrhythmic agent.

In some embodiments of the invention, the pharmacological agent comprises a statin selected from the group comprising atorvastatin, cerivastatin, fluvastatin, lovastatin, mevastatin, pitavastatin, pravastatin, rosuvastatin, and simvastatin.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
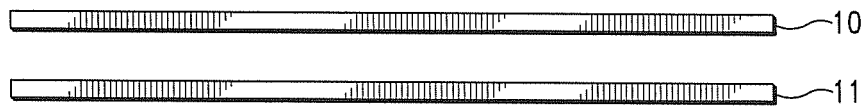
FIG. 1A is a front plan view of two sheets of extracellular matrix (ECM) that can be employed to form one embodiment of a multi-sheet extracellular matrix (ECM) structure, in accordance with the invention.
Figure 1B:
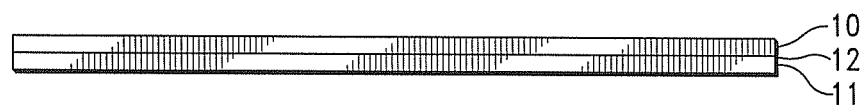
FIGS. 1B and 1C are front plan and perspective views, respectively, of a laminated multi-sheet ECM structure formed from the ECM sheets shown in FIG. 1A, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The term "adolescent", as used herein, means and includes a mammal that is preferably less than three (3) years of age.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omomentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The term "mesothelial tissue", as used herein, means and includes epithelium of mesodemial origin. As is well known in the art, mesothelial tissue includes many of the seminal components, e.g., GAGs, growth factors, etc, that are contained in ECM.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuception, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor-alpha (TGF-α), transforming growth factor-beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor-alpha (TNA-α), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/ enactins, fibulin I, finulin II, integrins, transmembrane molecules, thrombospondins, osteopontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V anti-arrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, al gestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to single and multi-sheet structures, i.e. grafts, for reconstructing or replacing damaged or diseased cardiovascular vessels.

In a preferred embodiment, the structures comprise extracellular matrix (ECM) derived from one or more than one tissue source in one or more donor mammals.

In some embodiments, the structures comprise a laminate of two or more sheets of extracellular matrix. Accordingly, two components of such a structure are first and second sheets of extracellular matrix, that are laminated together to form a laminate of extracellular matrix sheets.

The two sheets in this example can be from the same source of extracellular matrix, i.e. both or all from SIS from a pig. The sheets can also be from different tissue sources of extracellular matrix, for example the first sheet is SIS, and the second sheet is SS. Both the SIS and SS can be from the same species of mammal (e.g. pig) or each from a different species of mammal (SIS from pig, and SS from cow). If there are 3 sheets in the laminate article all 3 can be SIS, or the first sheet can be SIS, the second SS, and the third sheet can be SIS, for example. These three sheets can be from the same species of mammal, i.e. a pig, or different mammalian species, i.e. the SIS sheets can be from a pig and the SS sheet can be from a cow.

Advantages are to be derived from using sheets of extracellular matrix from different mammalian tissues, where, for example, each tissue source provides certain attributes. For example, SIS provides tensile strength and the kind of support to newly forming tissue that one would attribute to small intestine submucosa. Adding a sheet from a different tissue, for example one without the tensile strength, but with other regenerative attributes, for example liver basement membrane (LBM), can lend to the article that is a laminate of sheets, an advantageous quality, particularly when two such sheets are laminate together.

A sandwich configuration of such sheets can be formed, for example, with two outer sheets having relatively substantial tensile strength and an inner sheet of less strength having other attributes, such as LBM. According to the invention, a SIS-LBM-SIS sheet sandwich may provide the appropriate matrix for tissue regeneration for certain tissues in the body having certain requirements both for strength and regenerative potential.

In some embodiments, the structure comprises two sheets of extracellular matrix that are configured to encase a medical device, such as a pacemaker, or a composition. According to the invention, the composition can be any dispersible composition comprising biologically active or pharmacological agent, such as a cell or cells.

According to the invention, the cell or cells can comprise, for example, a plurality of stem cells that can aide and promulgate tissue regeneration from the article after placement in the patient. Thus, according to the invention, the sheets can comprise SIS and the composition can comprise LBM, or the sheets can be SIS and the gel composition can also be SIS.

For any of these structures, the sheets can be laminated to each other at the edges around an amount of composition that then becomes encased in the two sheets upon lamination of the outer sheets to each other. According to the invention, lamination of the two outer sheets together can be partial or complete, so that the composition can be entirely contained within the two sheets, or can be permitted to ooze out from between the sheets upon placement in the subject receiving treatment. The composition comprising the cells can also be a composition that supports the cells and allows them to survive and differentiate in that environment.

In another embodiment, the sheets can encase one or more cells. According to the invention, the cell or cells can comprise stem cells. The sheet sandwich can act as support for the growth and development of the cells once placed in the body. The cell or cells can advantageously work in the structure to regenerate tissue, or heal damaged tissue in conjunction with the extracellular matrix sheets.

According to the invention, the cell or cells can be part of a composition comprising such cells, such as cell media or other material that will help promote the cell survival and differentiation.

According to the invention, the cell in the composition can be any cell, such as, for example, a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell. This list is not intended to be exhaustive.

The composition comprising a cell or cells can comprise any material supportive of the purposes of the structure and cell culture, cell survival and differentiation. Thus, for example, the composition can comprise extracellular matrix that supports cells in culture and in vivo. The composition can comprise any material supportive of the purposes of the composition and the article in general, such as for example tissue regeneration, wound healing, cell culturing and survival, cell differentiation, stem cell recruitment and the like.

Any composition to support the cells, such as an extracellular matrix composition, can comprise such forms of extracellular matrix as an emulsion, gel, liquid, paste or particulate placed in between the sheets of matrix can be of mixed source of extracellular matrix, so that for example the gel can be a 50:50 mixture of LBM and UBS. The composition can also be a mixture of LBM and UBS. Thus, the composition can be some mixture or ratio of extracellular matrix from one or more tissue sources.

Generally, for any of the structures of the invention, the components, such as sheets of extracellular matrix, can be from the same mammalian tissue source (e.g. SIS) or they can be from different tissue sources (e.g. a SIS sheet and an LBM emulsion). Mammalian tissue sources are, in general, any tissue having an extracellular matrix that can be isolated from a mammal and decellularized. Thus, for example, most mammalian organs comprise tissue sources.

According to the invention, the tissue sources can be, for example, any mammalian tissue, including, but not limited to, the small intestine, large intestine, stomach, lung, liver, kidney, pancreas, placenta, heart, bladder, prostate, tissue surrounding growing tooth enamel, tissue surrounding growing bone, and any fetal tissue from any mammalian organ.

The forms of the extracellular matrices that make up the structures are generally sheets, although the sheets can be in any shape or size necessary for the site. Thus, for example, the sheets can be square, rectangular, triangular, or circular. The sheets can be large or small, depending once again on the site that the article is to be placed.

Placement of the structures in the patients can be accomplished by any reasonable means, including simply placing the article at the site of defect, or attaching the article in place, e.g. by glue or suture.

According to the invention, extracellular matrix can be obtained from the tissues of mammals by processes such as described in U.S. Pat. Nos. 5,554,389, 4,902,508 and 5,281,422. For example, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS). Obtaining enamel matrices is described in U.S. Pat. No. 7,033,611. Enamel matrix is extracellular matrix existing near forming teeth.

Other tissues, such as the liver and pancreas, have a basement membrane that does not demonstrate the kind of tensile strength of the tissues defined as submucosa. However, other useful properties may be opportunistically employed from the extracellular matrices of such tissues as the liver, pancreas, placenta and lung tissues, which have either basement membrane for extracellular matrix or interstitial membrane (as with the lung). These softer matrices support cells such as those in the organs from which the matrices are derived. Thus, certain benefits are to be found in using the extracellular matrices of these tissues, especially in combination with other such matrices like SIS and SS that may be stronger and which offer their particular advantages.

The extracellular matrices surrounding developing tooth enamel and developing bone also have particular advantages over other matrices in that they support the growth and differentiation of the hard tissues of bone and enamel.

Matrices can be used in whole or in part, so that for example, an extracellular matrix can contain just the basement membrane (or transitional epithelial layer) with the sub-adjacent tunica propria, the tunica submucosa, tunica muscularis, and tunica serosa. The matrix composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the matrix composition from any given source will contain the active extracellular matrix portions that support cell development and differentiation and tissue regeneration.

Thus, it is generally understood by persons of skill in the art that the extracellular matrix of any of the mammalian tissue consists of several basically inseparable layers broadly termed extracellular matrix. Where layers can be separated these separate layers can electively be included in the composition, depending on whether they serve the purpose that is the goal of the article being made.

The sheets can come from one or more sources of mammalian extracellular matrix. Thus, for example, the composition can comprise extracellular matrix combinations from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Generally, a given sheet will be of one source of extracellular matrix, but if the structure has two sheets, one sheet can be from one tissue source, and the second sheet can be from a second, different, tissue source.

According to some embodiments, the compositions of the invention can be made as follows: cells are selected for seeding and placing in between the sheets of extracellular matrix. The cell media is selected and the cells cultured to viability and then placed in the article.

In constructing the laminates, the ends of the sheets can be sealed using any reasonable means to do so, such as, for example, gluing or suturing the sheets to each other to form the article. If the sheets are encasing a composition comprising a cell or cells, the sheets are laminated at the outside edges and will encase the cells or cell composition. If a single sheet is folded over to encase a composition, lamination occurs on three sides of the sheet. If a rectangular or other-shaped structure is constructed from two or more sheets in a laminate, lamination occurs at the edges of the article to seal the composition inside, or to affix the sheets together.

For example, sheets can be laminated or layered with each other, so that a sheet of SIS can be placed with a sheet of SS, either with two sheets together SIS-SS or as a sandwich with three sheets, for example SIS-SS-SIS. Also, a different sandwich configuration can be made with two sheets of SIS or SS, sandwiching a gelatinous semi-solid or a solid powder (particulate) form of the matrix. The sandwich can be closed so that a composition can be placed securely between the two outer sheets. A single sheet can alternatively be folded over to encase an amount of composition.

Turning now to the figures, FIG. 1 depicts the laminate sheets in a rectangle shape, and circular and triangle shapes. FIG. 1A depicts a first rectangular sheet 10 and second rectangular sheet 11, before lamination. FIG. 1B depicts rectangular sheet 10 and rectangular sheet 11 laminated together to form laminated structure 12.

Figure 1C:
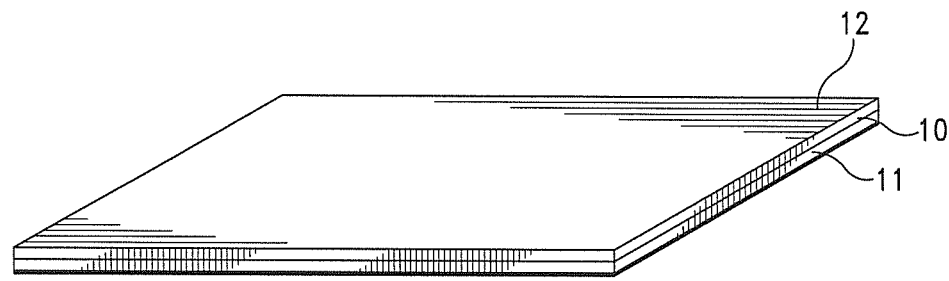
Figure 1D:
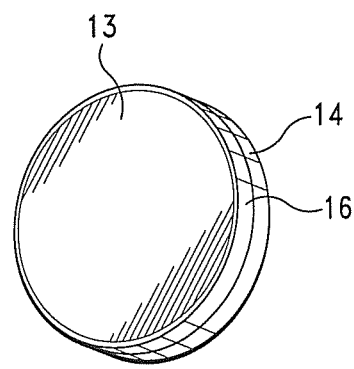
FIG. 1D is a perspective view of a round laminated multi-sheet ECM structure, in accordance with the invention.
Figure 1E:
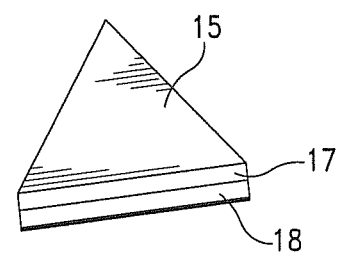
FIG. 1E is a perspective view of a triangular shaped laminated multi-sheet ECM structure, in accordance with the invention.

FIG. 1C depicts laminated article 12, having sheets 10 and 11 laminated together in a 3-dimensional perspective to form rectangular laminated article 12. FIG. 1D depicts circular laminated article 13 having laminated circular sheets 14 and 16 laminated together. FIG. 1E depicts laminated article 15 having a triangular shape, formed by lamination of triangular sheets 17 and 18 being laminated together.

Figure 2A:
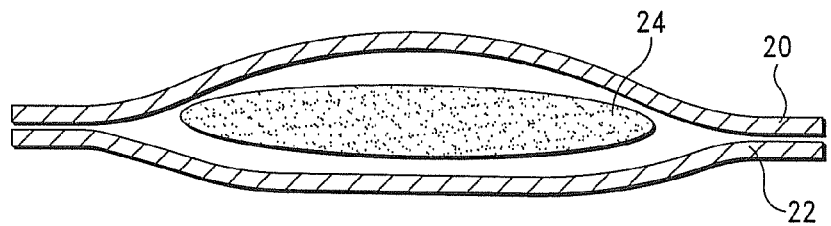
FIGS. 2A and 2B are front sectional views of a laminated multi-sheet ECM structure having an ECM composition disposed in the ECM article internal cavity, in accordance with the invention.
Figure 2B:
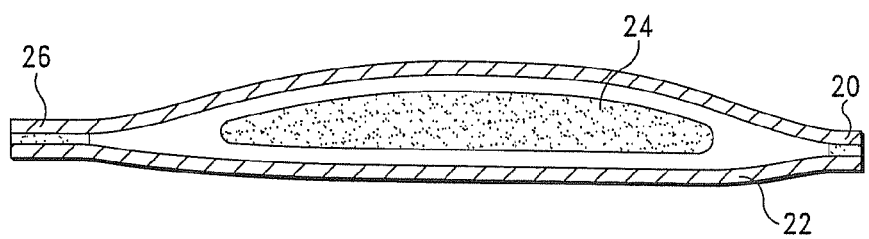

FIG. 2A depicts two sheets, a top sheet 20 and a bottom sheet 22, overlaying a composition 24. FIG. 2B depicts a cross sectional view of the top sheet 20 and bottom sheet 22 laminated at point 26 to encase composition 24.

Figure 2C:
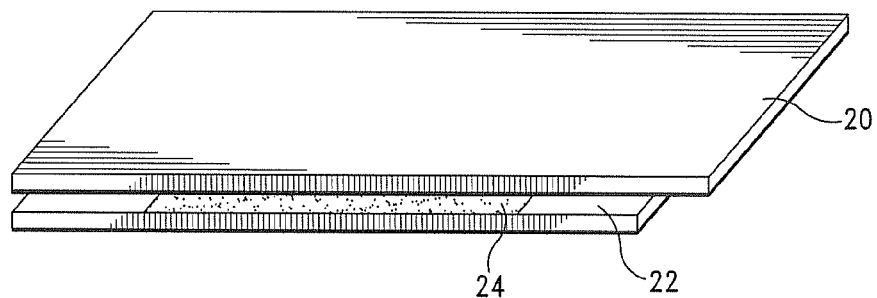
FIGS. 2C and 2D are perspective views of ECM sheets with an ECM composition disposed therebetween, in accordance with the invention.
Figure 2D:
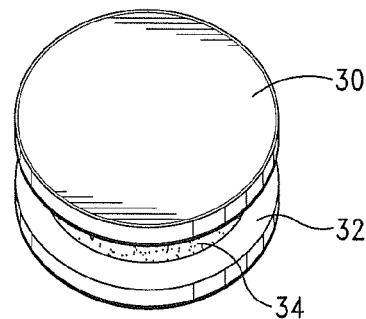

FIG. 2C depicts a 3-dimensional view of top sheet 20 and bottom sheet 22 with composition 24 in between the two sheets prior to lamination. FIG. 2D depicts a circular structure having top sheet 30 and bottom sheet 32 with composition 34 therebetween.

Figure 3A:
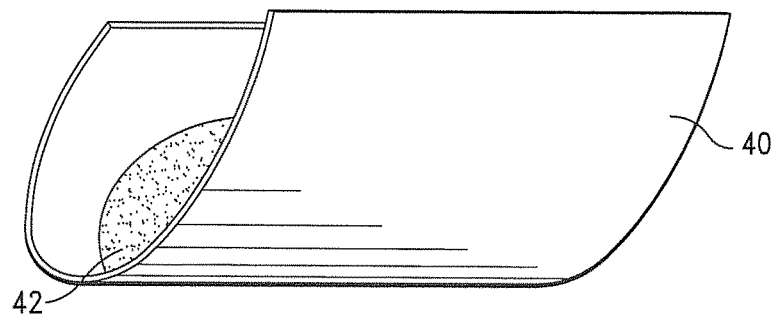
FIGS. 3A-3C are perspective views of a folded ECM sheet with an ECM composition disposed therebetween, in accordance with the invention.
Figure 3B:
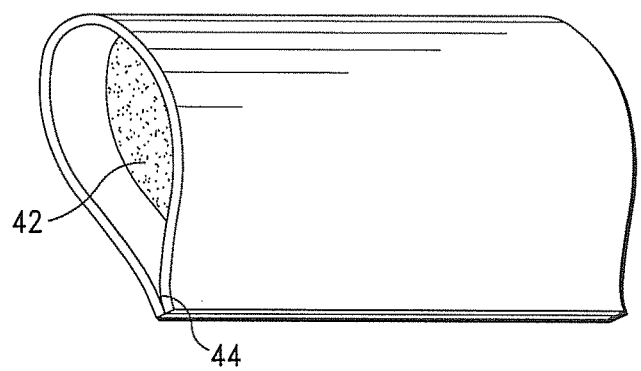
Figure 3C:
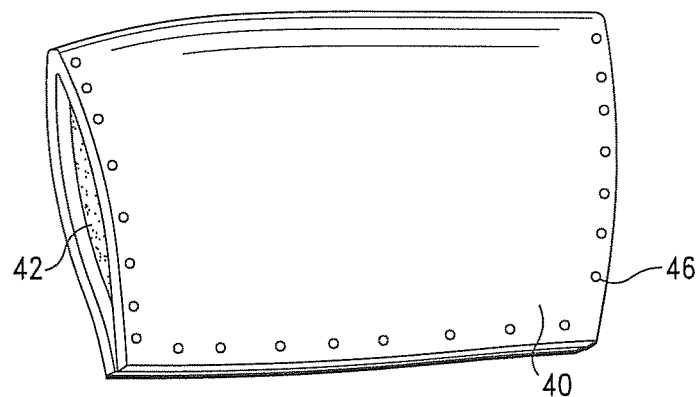

FIG. 3A depicts single folded sheet 40 encasing composition 42. FIG. 3B depicts single sheet 40 encasing composition 42 with laminated edge 44. FIG. 3C depicts single sheet 40 having composition 42 with laminate points 46 on three (3) sides of the structure.

As indicated above, according to the invention, the laminate structure can encase a composition comprising a cell or a plurality of cells, and a material that supports the culturing of the cells. The composition can also comprise extracellular matrix in gel or emulsion form that supports cell growth and survival.

According to the invention, the composition can further comprise an additional component, such as a component that serves the composition and its purpose in the mammalian body. Thus, the additional component can facilitate the regeneration of tissue, healing of a wound, cultivation of cells in the composition, enhanced recruitment endogenous stem cells once in the body, modulation of the immune environment, therapeutic treatment, or otherwise contribute to some aspect of the process for which the composition and article that includes the composition is being used.

The additional component can thus comprise a protein. The protein can be for example a growth factor, or any other type or protein that might stimulate some part of the tissue regenerative process, including, without limitation, a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF). This list is not intended to be exhaustive.

Figure 4A:
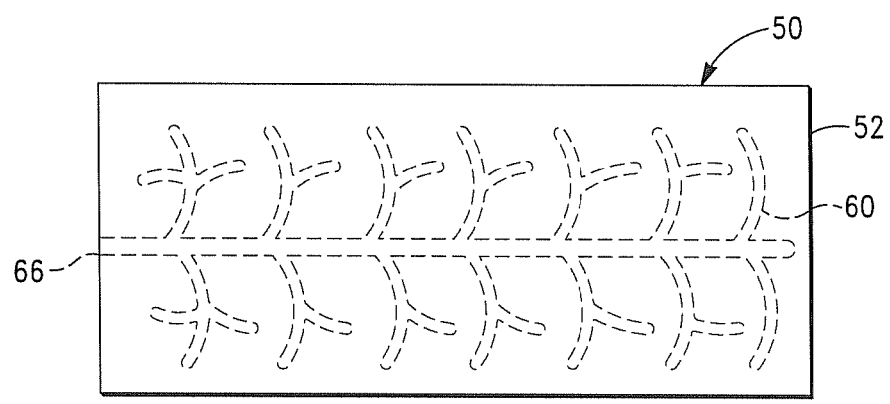
FIG. 4A is a top plan view of embodiment of a multi-sheet extracellular matrix (ECM) structure having an agent dispersal network therein, in accordance with the invention.
Figure 4B:
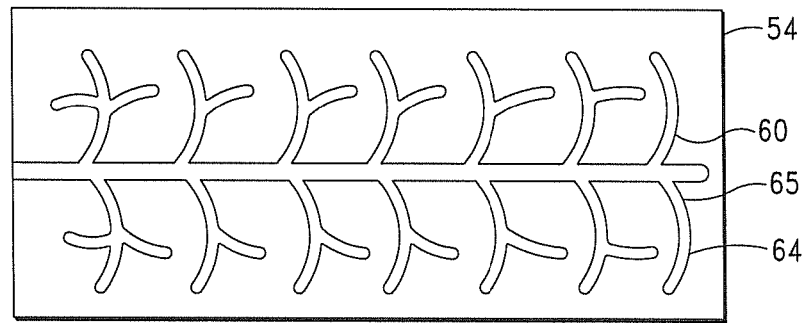
FIG. 4B is a top plan view of the bottom sheet of the multi-sheet extracellular matrix (ECM) structure shown in FIG. 4A, showing the network channels disposed on the top surface, in accordance with the invention.
Figure 4C:
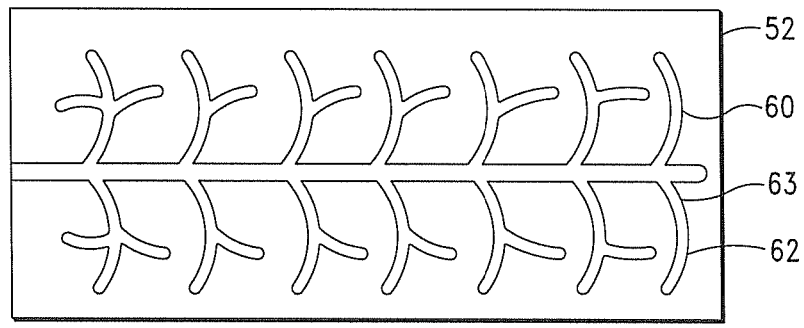
FIG. 4C is a top plan view of the top sheet of the multi-sheet extracellular matrix (ECM) structure shown in FIG. 4A, showing the network channels disposed on the bottom surface, in accordance with the invention.

Referring now to FIGS. 4A4C, there is shown another embodiment of an ECM structure of the invention (denoted generally "50"). As illustrated in FIGS. 4A and 4C, the ECM structure 50 comprises a multi-sheet structure having top 52 and bottom 54 sheets, and an agent dispersal network 60 disposed therebetween.

As indicated above, the network 60 is configured to receive and disperse at least one bioactive agent or composition therefrom, where, when the ECM structure 50 is disposed on target tissue, the bioactive agent is administered thereto. According to the invention, the bioactive agent or composition can comprise any of the aforementioned compositions. The bioactive agent can also comprise any of the aforementioned biologically active and pharmacological agents.

In a preferred embodiment of the invention, the structure sheets 52, 54 similarly comprise ECM from a mammalian tissue source. According to the invention, the ECM tissue source can comprise any of the aforementioned tissue sources, e.g. SIS, LBM, mesothelial tissue, etc. In a preferred embodiment, the ECM is derived from an adolescent tissue source.

The ECM can also additionally comprise one or more of the aforementioned biologically active or pharmacological agents or compositions.

Referring now to FIGS. 4A-4C, there is shown another embodiment of an ECM structure of the invention (denoted generally "50"). As illustrated in FIGS. 4A and 4C, the ECM structure 50 comprises a multi-sheet structure having top 52 and bottom 54 sheets, and an agent dispersal network 60 disposed therebetween.

According to the invention, the ECM can comprise additional sheets, e.g., one or more additional sheets disposed on the top 52 sheet.

As indicated above, the network 60 (and network member 72, discussed below) is configured to receive and disperse at least one bioactive agent or composition (in liquid form) therefrom, wherein, when the ECM structure 50 is disposed on target tissue, the bioactive agent is administered thereto.

According to the invention, the bioactive agent or composition can comprise any of the aforementioned biologically active and pharmacological agents and compositions. The bioactive agent can also comprise any of the aforementioned biologically active and pharmacological agents.

In some embodiments, the bioactive agent comprises a statin selected from the group comprising atorvastatin, cerivastatin, fluvastatin, lovastatin, mevastatin, pitavastatin, pravastatin, rosuvastatin and simvastatin.

In some embodiments, the bioactive agent comprises saline or sterile water.

In a preferred embodiment of the invention, the structure sheets 52, 54 similarly comprise ECM from a mammalian tissue source. According to the invention, the ECM tissue source can comprise any of the aforementioned tissue sources, e.g. SIS, LBM, mesothelial tissue, etc. In a preferred embodiment, the ECM is derived from an adolescent tissue source.

The ECM can also additionally comprise one or more of the aforementioned biologically active or pharmacological agents or compositions.

Referring to FIGS. 4B and 4C, in some embodiments, the agent dispersal network 60 comprises mating channels 62, 64 between two sheets, i.e. an upper portion of the network 60 (denoted "63") being disposed in a first sheet, i.e. sheet 52, and a lower portion of the network 60 (denoted "65") being disposed in a second mating sheet, i.e. sheet 54. According to the invention, the mating channels 62, 64 can be formed in the sheets by any conventional means.

Figure 4D:
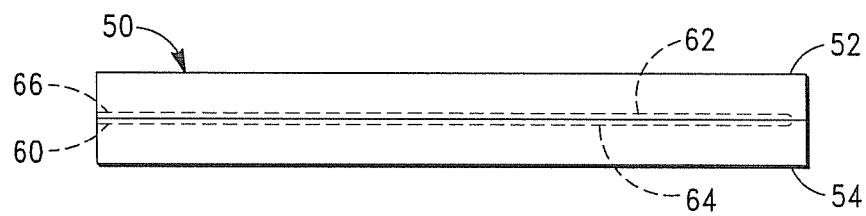
FIG. 4D is a front plan view of the multi-sheet ECM structure shown in FIG. 4A, in accordance with the invention.
Figure 4E:
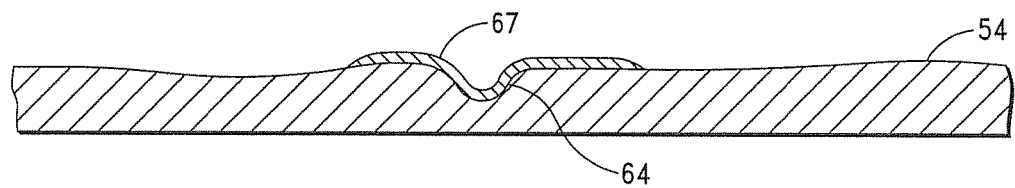
FIG. 4E is a side sectional plan view of the bottom sheet of the multi-sheet extracellular matrix (ECM) structure shown in FIG. 4A, showing coated network channels, in accordance with the invention.

Referring now to FIG. 4E, in some embodiments of the invention, each channel 62, 64 further comprises a flexible permeable liner or membrane (or coating) 67 to maintain the structural integrity of the channels 62, 64. Preferably, the liner or coating comprises a bioresorbable, liquid (e.g., $H^2O$) permeable material. According to the invention, suitable liner or coating materials include, without limitation, bioresorbable polymeric materials, such as polycaprolactone (PCL) and polyhydroxybutyrate (PHB).

Figure 5A:
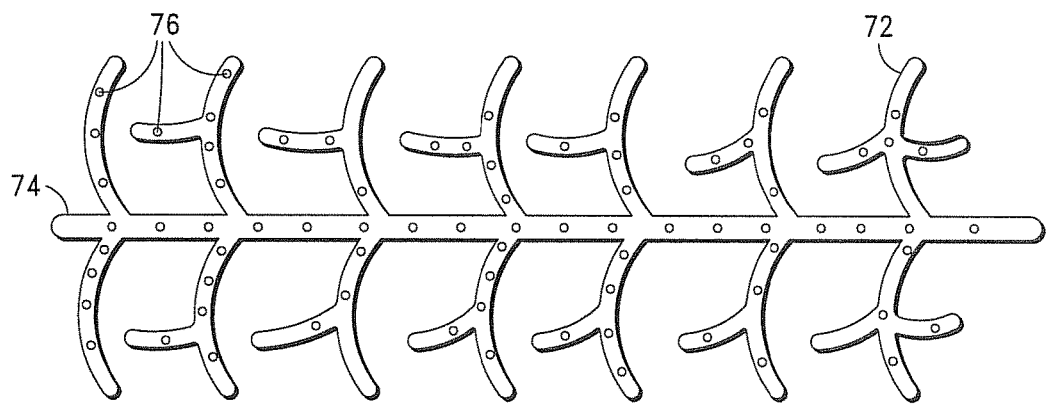
FIG. 5A is a top plan view of one embodiment of an agent dispersal network member, in accordance with the invention.

According to the invention, the agent dispersal network 60 is preferably continuous and can comprise various configurations and sizes. The network configuration shown in FIGS. 4A, 4B and 5A is thus merely one network configuration that can be employed within the scope of the invention and, hence, should not be deemed limiting in any manner.

As illustrated in FIGS. 4A and 4D, in some embodiments, the network 60 includes at least one open region (or opening) 66 when the mating sheet members 52, 54 are joined. The opening 66 is preferably sized and configured to allow ingress of a composition and/or biologically active or pharmacological agent of the invention into the network 60.

Figure 7:
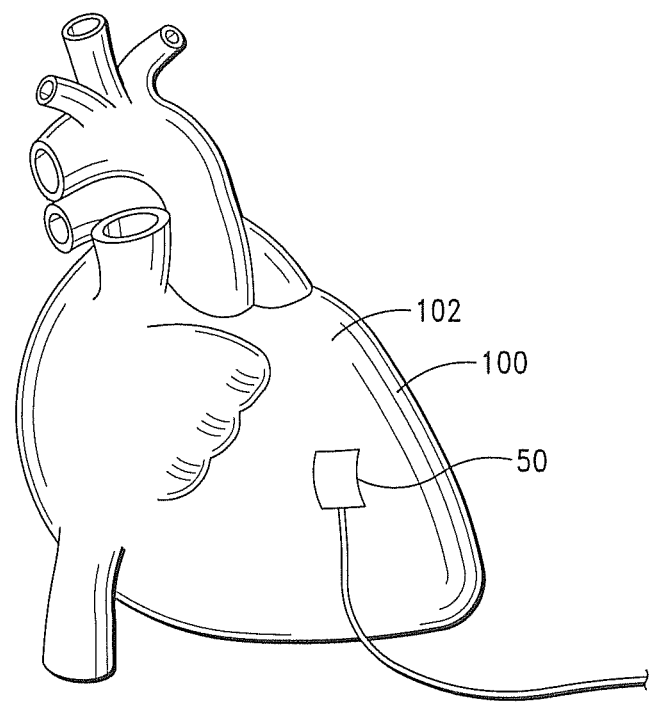
FIG. 7 is an illustration of a multi-sheet ECM structure placed on the heart of a subject, in accordance with the invention.

According to the invention, the composition and/or biologically active or pharmacological agent can be provided to the network 60 via a separate agent delivery line 80 that is configured to communicate with the opening 66. Preferably, the delivery line 80 has sufficient length to extend outside the body when the structure 50 is placed on target tissue within the body, e.g. the myocardium 102 of a heart 100, as illustrated in FIG. 7.

In some embodiments of the invention, the agent dispersal network 60 comprises a sealed structure having a composition and/or biologically active or pharmacological agent of the invention disposed in the network 60 by, for example, suturing and, hence, closing the network opening 66 after the desired composition and/or biologically active or pharmacological agent is disposed therein.

Figure 5B:
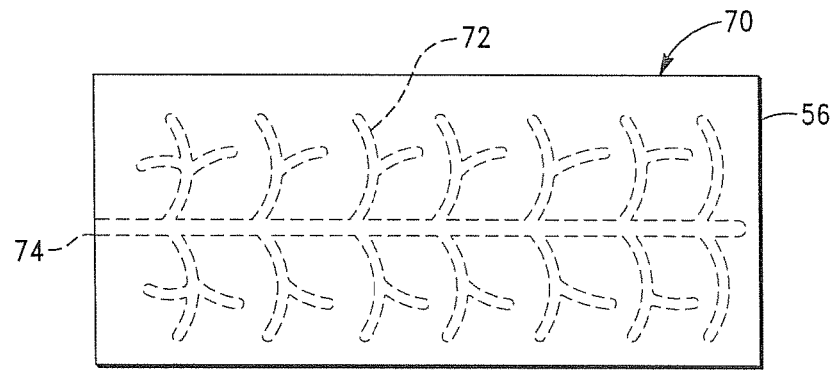
FIG. 5B is a top plan view of a multi-sheet ECM structure having the agent dispersal network member shown in FIG. 5A disposed between two sheets.

Referring now to FIGS. 5A and 5B, in some embodiments, the agent dispersal network comprises a separate porous network member 72 that is configured to be disposed between two sheets (sheet 56 shown in FIG. 5B) to form an ECM structure 70.

As illustrated in FIG. 5A, the network member 72 similarly includes at least one opening 74 that is sized and configured to allow ingress of a composition and/or biologically active or pharmacological agent of the invention into the network member 72.

In some embodiments, the network member 72 comprises a porous structure, such as, by way of example, a polymer mesh. The porous structure can further comprise a plurality or pores 76, such as shown in FIG. 5A.

In some embodiments of the invention, the network member 72 has a configuration that can be readily removed from the structure after a predetermined period of time.

According to the invention, the network member 72 can comprise various biocompatible materials. In a preferred embodiment, the network member 72 comprises a biocompatible and biodegradable material.

In some embodiments, the biodegradable material comprises a biodegradable polymeric material selected from the group comprising polyhydroxyalkonates (PHAs), polylactides (PLLA) and polyglycolides (PLGA) and their copolymers, for example poly(ε-caprolactone-co-glycolide), polyanhydrides, and like polymers.

In some embodiments, the biodegradable material comprises an ECM structure comprising at least one of the aforementioned ECM materials.

Figure 6:
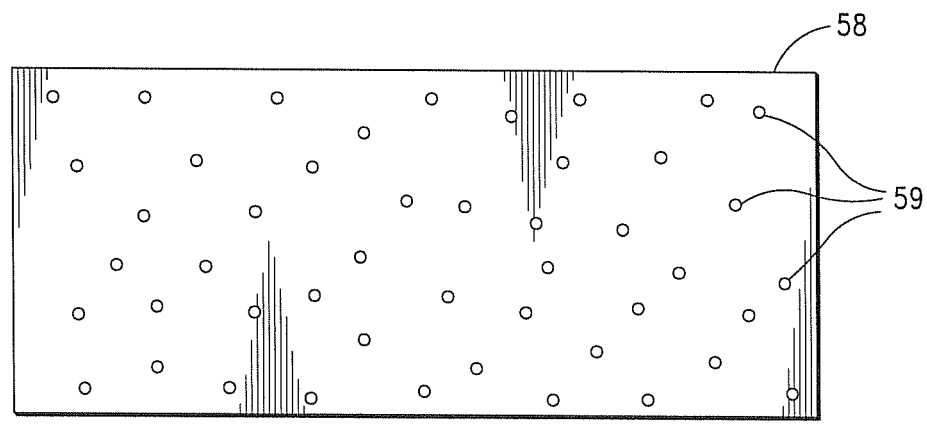
FIG. 6 is a top plan view of a porous ECM sheet, in accordance with the invention.

According to the invention, the ECM sheets employed to form the ECM structures 50, 70 can comprise any form. Thus, in some embodiments, at least one sheet, more preferably, each joined sheet embodying a network structure of the invention, comprises a porous structure, such as porous sheet structure 58 shown in FIG. 6, wherein the porous structure comprises a plurality of pores 59, or a mesh structure. According to the invention, porous sheet structure facilitates the delivery of a desired composition and/or biologically active or pharmacological agent of the invention from the network (i.e. network 50 and/or network member 72 to tissue when the ECM structure is disposed thereon.

According to the invention, the porosity of the channel coating (or film) 67, network member 72 and ECM sheets (e.g. sheets 52, 54 and 58) can be tailored to provide a desired biologic agent administration rate to tissue when an ECM structure of the invention, such as structures 50 and 70, are in communication therewith.

As indicated above, in addition to administering a desired composition and/or biologically active or pharmacological agent of the invention to target tissue, the ECM structures of the invention, also induce neovascularization and remodeling of tissue, when disposed thereon.

Without departing from the spirit and scope of this invention, one of ordinary skill can make various changes and modifications to the invention to adapt it to various usages and conditions. As such, these changes and modifications are properly, equitably, and intended to be, within the full range of equivalence of any subsequently proffered claims.

What is claimed is:
1. An extracellular matrix (ECM) structure for tissue regeneration, comprising:
   a multi-sheet structure comprising a first sheet member having first top and bottom surfaces and a second sheet member having second top and bottom surfaces, said first and second sheet members being joined proximate said first sheet member first bottom surface and said second sheet member second top surface,
   said first and second sheet members comprising an ECM composition comprising decellularized ECM derived from small intestine submucosa (SIS), said decellularized ECM comprising endogenous glycosaminoglycans (GAGs), transforming growth factor-beta (TGF-β), fibroblast growth factor-2 (FGF-2) and vascular epithelial growth factor (VEGF),
   said multi-sheet structure being configured to modulate inflammation of damaged tissue and not elicit an adverse inflammatory response of said damaged tissue, and induce neovascularization, host tissue proliferation, bioremodeling of said damaged tissue and regeneration of new tissue and tissue structures with site specific structural and functional properties, when said multi-sheet structure is delivered to said damaged tissue; and
   an agent dispersal network member comprising a biodegradable polymeric material, said agent dispersal network member being disposed between said first and second sheet members proximate said first sheet member first bottom surface and said second sheet member second top surface, said agent dispersal network member comprising a sealed, continuous structure comprising a plurality of mating channels that are configured to receive a bioactive agent therein and disperse said bioactive agent into said first and second sheet mem- bers, wherein, when said multi-sheet structure is delivered to said damaged tissue, said bioactive agent is transferred thereto.

2. The ECM structure of claim 1, wherein said agent dispersal network member further comprises at least one opening that is in communication with said mating channels.

3. The ECM structure of claim 1, wherein said agent dispersal network member comprises a porous network member having a continuous lumen that is configured to receive and transfer said bioactive agent therein, and disperse said bioactive agent therefrom.

4. The ECM structure of claim 3, wherein said biodegradable polymeric material comprises a polymeric material selected from the group consisting of polyhydroxyalkonates (PHAs), polylactides (PLLA), polyglycolides (PLGA) and polyanhydrides.

5. The ECM structure of claim 1, wherein said ECM composition further comprises at least one exogenously added biologically active agent.

6. The ECM structure of claim 5, wherein said biologically active agent comprises fibroblast growth factor-2 (FGF-2).

7. The ECM structure of claim 1, wherein said first sheet member further comprises a porous structure.

8. The ECM structure of claim 1, wherein said second sheet member further comprises a porous structure.

\* \* \* \* \*